United States Patent [19]

Leonard

[11] Patent Number: 5,052,554

[45] Date of Patent: Oct. 1, 1991

[54] DENTAL IMPRESSION MATERIAL PACKAGE AND METHOD

[76] Inventor: Peter H. Leonard, 3680 Woodside Dr., Columbus, Ind. 47203

[21] Appl. No.: 449,808

[22] Filed: Dec. 13, 1989

[51] Int. Cl.[5] .................... B65D 30/28; B65D 17/28; B65D 25/08

[52] U.S. Cl. .................................. 206/219; 206/632; 383/906; 383/907

[58] Field of Search ............... 206/632, 601, 222, 219; 383/35, 906, 907

[56] References Cited

U.S. PATENT DOCUMENTS

| | | | |
|---|---|---|---|
| 2,568,913 | 9/1951 | Friedman | 206/219 X |
| 2,598,595 | 5/1952 | Peters | 206/219 X |
| 2,675,957 | 4/1954 | Zimmerman | 383/35 |
| 2,935,241 | 5/1960 | Brady | 383/907 X |
| 3,064,802 | 11/1962 | Jess et al. | 206/219 |
| 3,172,796 | 3/1965 | Gulker | 383/907 X |
| 3,208,102 | 9/1965 | Rubio | 206/219 X |
| 3,261,381 | 7/1966 | Roach | 206/219 X |
| 3,608,709 | 9/1971 | Pike | 206/219 |
| 3,756,571 | 9/1973 | Winberg | 206/221 |
| 3,785,111 | 1/1974 | Pike | 383/37 X |
| 3,807,118 | 4/1974 | Pike | 206/632 X |
| 4,023,675 | 5/1977 | Claasen | 206/219 |
| 4,282,863 | 8/1981 | Beigler et al. | 604/262 |
| 4,336,802 | 6/1982 | Stone et al. | 604/414 |
| 4,441,538 | 4/1984 | Larkin et al. | 215/247 X |
| 4,458,733 | 7/1984 | Lyons | 141/1 |
| 4,516,977 | 5/1985 | Herbert | 604/415 |
| 4,549,657 | 10/1985 | Martin | 383/35 X |
| 4,795,271 | 1/1989 | Lane, Jr. et al. | 206/632 X |

Primary Examiner—Paul T. Sewell
Assistant Examiner—Jacob K. Ackun, Jr.
Attorney, Agent, or Firm—Woodard, Emhardt, Naughton, Moriarty & McNett

[57] ABSTRACT

A flat plastic bag of generally triangular configuration is factory-filled with a measured amount of dental impression powder. The sealed bag has a frangible seam pierceable intentionally by a conventional syringe nozzle to add water when ready to mix. A corner of the bag opposite this seam is severed, when desired, to for controlled dispensing of the contents into an impression tray. In use, a measured amount of water in the syringe bulb is introduced to the bag by insertion of the bulb nozzle into the seam margin. Then the bag is gripped between the pierced opening and the top of the water and powder contained in the bag. Then the water and powder are mixed by kneading the bag. When mixing is complete, the dispenser corner of the bag is severed, and the material is squeezed into the impression tray. Before introduction of water into the bag, the bag is essentially flat except where deformed by the powder itself, thus minimizing air in the bag. During introduction of water, the bag expands as needed to receive the water, but introduciton of air still is avoided. The mixture is delivered from the severed corner of the bag into the impression tray without creation of air pockets and without air bubbles entrained in the mixture.

4 Claims, 3 Drawing Sheets

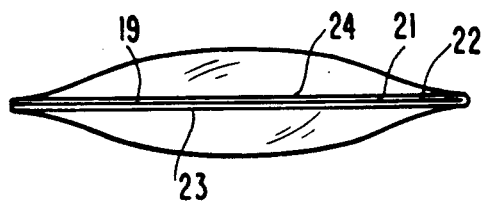
Fig.2
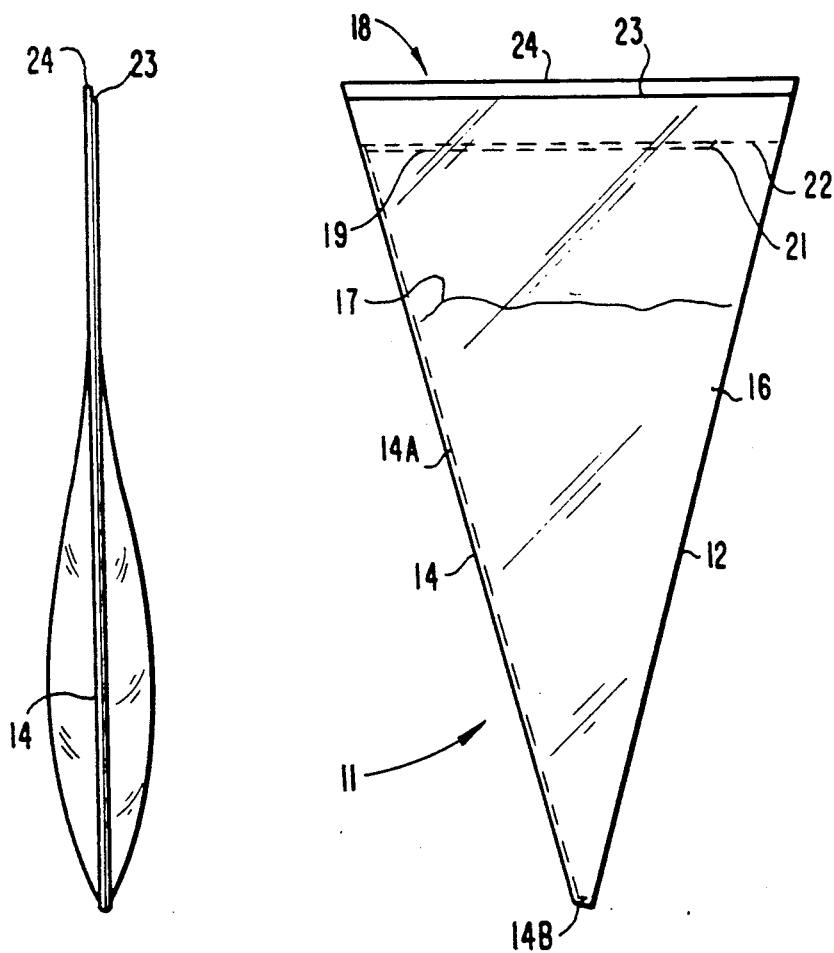
Fig.3  Fig.1  Fig.4

DENTAL IMPRESSION MATERIAL PACKAGE AND METHOD

BACKGROUND OF THE INVENTION

This invention relates generally to dentistry, and more particularly to the preparation of material for making dental impressions.

DESCRIPTION OF THE PRIOR ART

For many years, an alginate material for making dental impressions has been sold in bulk containers to the dentist. To prepare it for use, the dental technician would shake the container to loosen the material which may have become packed in shipment or daily storage. Then, using a rubber bowl, the technician would measure a couple of scoops of powder into the bowl, introduce a measured amount of water, and begin mixing with a spatula. When the material was thoroughly mixed, it was then spooned from the bowl with the spatula into a dental impression tray. Then it was used by the dentist to make the impression. During the mixing step, and during transfer to the impression tray, air was introduced even though care was taken to avoid it. Air is undesirable because air bubbles in the mixture detract from the quality of the impression that can be made in the material. Also, since the material sets rather quickly, and some time must be allowed for the dentist to position the tray properly, considerable care and skill in the mixing process was desirable. Finally, after the material was used, and the impression was made and set, there remained the matter of cleaning up the bowl, the spatula, the impression tray, and the sink and any powder that was spilled during the initial steps of the procedure. Also, since the powder is very fine, careless handling of it can create an undesirable risk of inhaling it.

I have previously improved the practice, by putting a pre-measured amount of impression powder in a plastic bag and, when ready for mixing, pouring water into the bag, gripping the bag to hold it closed, and then kneading the bag to mix the contents. Then the material would be squeezed from the bag into the impression tray.

Since making my present invention, I have learned of a prior art U.S. Pat. No. 4,023,675, issued May 17, 1977 to Claasen. That patent shows packaging with preserved sterile water in one compartment and powdered impression material in the other. The compartments are separated by a labyrinth type of fold in the packaging material which is clamped together to maintain that separation until use. There has remained a need for a system which avoids the necessity of packaging and shipping water and which can be readily used without any special tools or equipment in the dentist's office.

SUMMARY OF THE INVENTION

A plastic bag of generally triangular configuration is factory-filled with a measured amount of dental impression powder and then sealed. The bag has a seam which can be readily pierced intentionally by the nozzle of a conventional syringe. A corner of the bag opposite this seam is severable, when desired, to permit controlled dispensing of the contents into an impression tray. When the package is to be used according to my method, a measured amount of water in the syringe is introduced to the bag by insertion of the nozzle into the seam margin. Then the bag is gripped between the pierced opening and the surface of the water now contained in the bag. Then the water and powder are mixed by kneading the bag. When the mixing is complete, the dispenser corner of the bag is severed, and the mix is squeezed into the impression tray. As initially provided, before introduction of water into the bag, the bag is essentially flat except as and where deformed by the powder itself, thus essentially eliminating all air from the bag. During the introduction of water, the bag will expand as needed to accommodate the water, but introduction of air still is avoided. The same is true during the kneading process. Also, since the bag is entirely full of the water and impression material mixture, it can be delivered in a continuous flow from the severed corner of the bag and directed into the impression tray without creation of air pockets and without air bubbles entrained in the mixture.

BRIEF DESCRIPTION OF THE DRAWINGS

FIG. 1 is a front elevational view of a package of dental impression powder according to a typical embodiment of my invention.

FIG. 2 is a top plan view thereof.

FIG. 3 is a left side elevational view thereof.

FIG. 4 is a right side elevational view thereof.

DESCRIPTION OF THE PREFERRED EMBODIMENT

Figure 5:
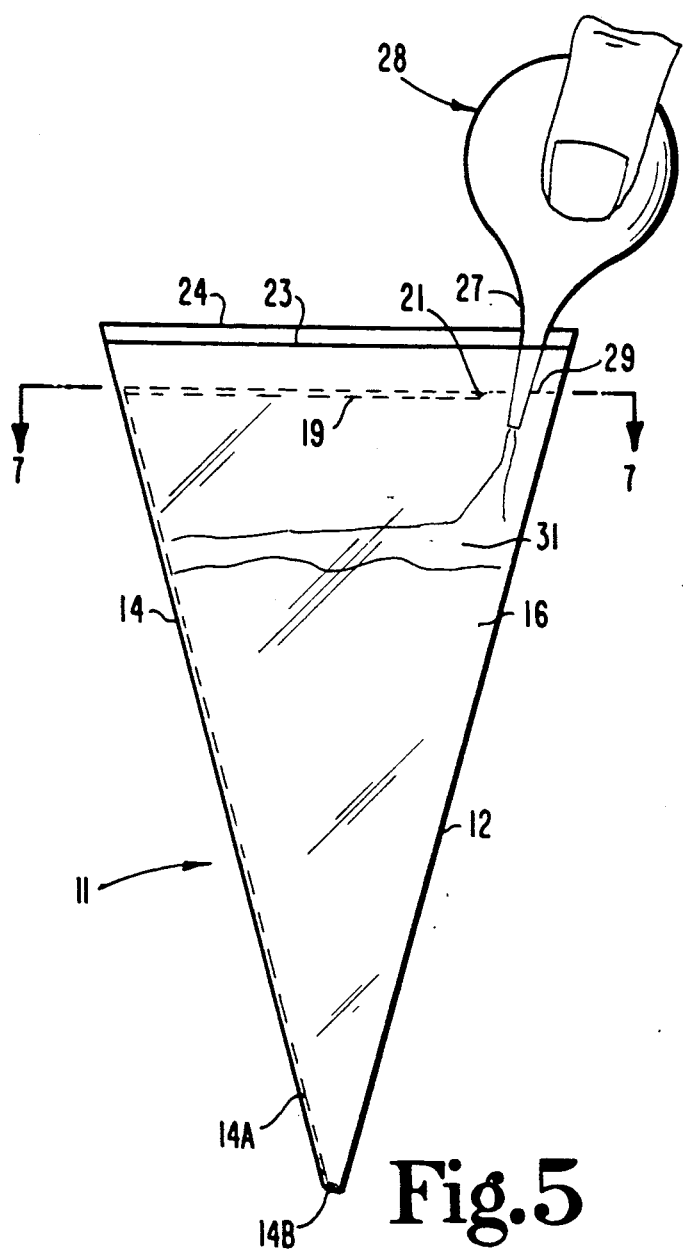
FIG. 5 is a view similar to FIG. 1 but showing the introduction of water into the bag.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, the package 11 may be made of a transparent plastic film strip folded upon itself along the line 12 with the overlying portions thereof being heat welded together along lines 14A and 14B. After filling with the dental impression powder 16, to about a level 17, the facing portions of the sheet are welded together at their upper margins 18 along a line 19 beginning at the line 14A and continuing to a jog in the line at 21 and continuing at 22 to the fold line 12. The upper edge 23 of the front panel is slightly (about 5 millimeters) lower than the upper edge 24 of the rear panel to make it easy to separate these edges adjacent the upper weld line 19, 21, 22. The weld along the lines 14A and 14B is very sturdy as is true also along and above line 19 where there are two dotted lines to indicate a heavy weld. However, at the jog at 21, the weld line is not so heavy for a distance of about 13 mm as indicated by the single dotted line at 22.

The contents of the bag are sealed inside the bag due to all the welds. Before filling, the bag is flat. It is an object to minimize introduction of air at all times. Therefore, the bag remains essentially flat after the introduction of the powder except to the extent that it is expanded by the bulk of the powder, and there is essentially no air in the bag over the top 17 of the powder as shown by the thin section in the end view of FIGS. 3 and 4 above this level.

Figure 6:
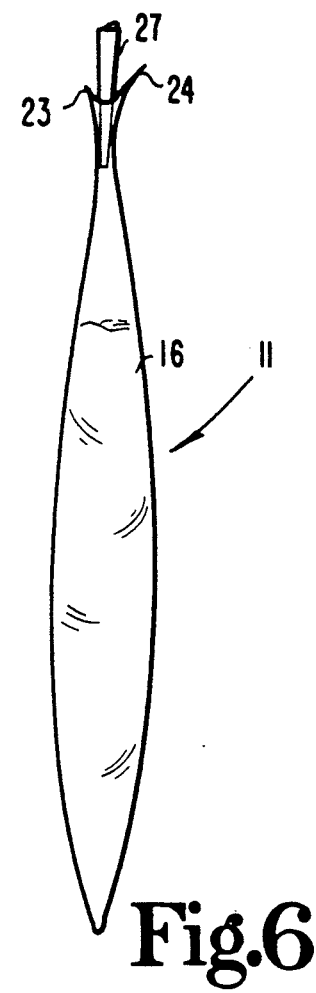
FIG. 6 is a view similar to FIG. 4 showing the introduction of water.
Figure 7:
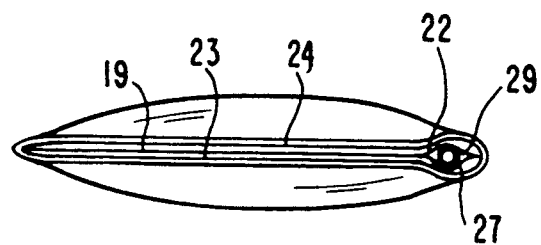
FIG. 7 is a horizontal section taken at line 7—7 in FIG. 5, viewed in the direction of the arrows and showing the syringe nozzle in cross section and showing the opening made in the sealed upper margin of the package during introduction of water.
Figure 8:
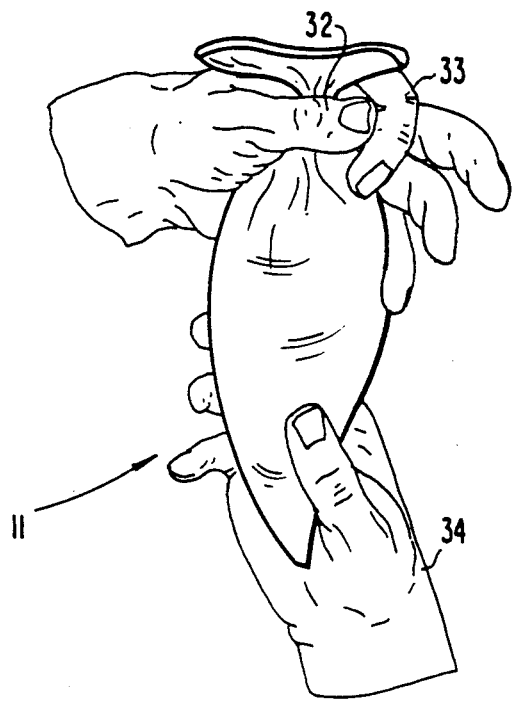
FIG. 8 is a pictorial view of the package being squeezed and kneaded for the mixing.
Figure 9:
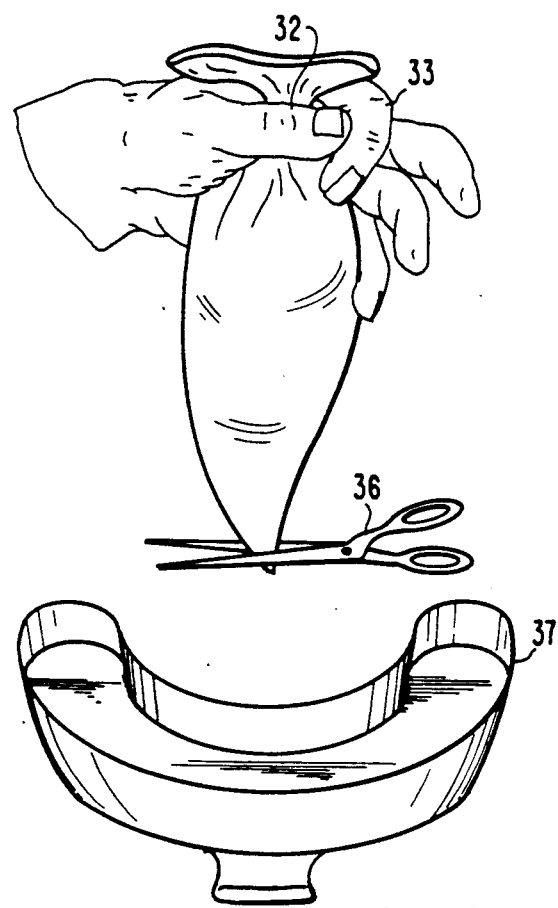
FIG. 9 is a pictorial view showing the lower end of the package being snipped off for dispensing the contents into the dental impression tray.

When the user is ready to add the water for mixing the powder, it is done by first puncturing the seal provided by the weld at line 22. This is accomplished as shown in FIGS. 5, 6 and 7 where the tapered nozzle 27 of the syringe 28 is pushed through the weld at line 22 to split it open as shown at 29 in FIG. 7, whereupon the water is squeezed from the syringe into the bag at 31 on top of the powder 16. When the desired amount of water has been added, the bag may be gripped between the thumb 32 and forefinger 33 of the left hand at a level on the bag immediately above the water and below the line 19. As the bag is held snugly by the left hand, it is kneaded by the right hand 34. In this way, the water and powder can be thoroughly mixed without squirting it back out through the opening 29, and without the introduction of air into the mixture.

When the kneading is finished so that the impression material is thoroughly mixed, the lower end portion of the bag can be snipped off as by a scissors 36 and then the material can be dispensed into the dental impression tray 37. When the desired amount of material has been squeezed into the tray, the bag can be discarded. Therefore, the only item which must be cleaned after use is the dental impression tray. There is no dust, mixing bowl, spatula, or scoop to be cleaned.

It can be noted that the edge 14 near the bottom tip of the package jogs sharply to the right at the weld line 14B. This portion is at right angles to the fold line 12 and may facilitate manufacture. The location above line 14B at which this lower corner of the generally triangular package may be cut off, will be determined by the user, depending upon the amount of material to be dispensed and the rate at which the user desires to dispense it. The optimum location may be such as to provide a substantially round discharge opening of approximately six millimeters diameter as the mixed material is squeezed out of the bag into the impression tray.

The size of the bag will depend on the amount of material to be mixed in it. In the conventional practice, where material is scooped from the bulk container, two scoops of approximately one tablespoon size are used for a standard adult-size impression tray. Occasionally, more material is used for larger trays, and less may be used for smaller trays, as for children. The amount of water to be used depends upon the requirement of the manufacturer of the powder, and based upon the amount of powder involved and the setting time desired. The desired amount of water can be drawn into the syringe from a measuring cup or graduate or beaker for discharge into the package when the mixing is to be done. As alternatives, the syringe itself may have a bulb sized to hold just the right amount of water or it may be of the cylinder-with-plunger type and have graduations on the cylinder, so the water can be drawn from any convenient source.

The material for the bag is preferably a good quality plastic material such as low-density polyethylene 0.5 to 1 mils thick. An example of the alginate powder is Jeltrate brand, alginate impression material, Type 1-Fast Set by The L. D. Caulk Division of Dentsply International Inc. of Milford, Del. Examples of bag dimensions for a two-tablespoon powder content would be about 12 cm across the top edge and about 20 cm along the sides 12 and 14 with edge 24 about 5 mm above edge 23, and edge 23 about 13 mm above the weld line 19, 21, 22.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A dental impression powder package comprising:
   a generally flat bag of generally triangular configuration having a top and two sides;
   dental impression powder in the bag and causing the bag to bulge as and where dictated by the amount of powder in the bag, but the bag being otherwise substantially flat;
   the top of said bag being sealed closed along a seal line formed to provide a relatively strong seal along most of the line but having a short portion of the seal line weaker than the remainder of the seal and frangible upon intentional puncturing with a syringe nozzle to facilitate adding water to the powder.

2. The package of claim 1 and wherein:
   the frangible portion is a heat welded seam.

3. The package of claim 2 and wherein:
   the frangible portion is about thirteen millimeters and adjacent the intersection of the top and one of said sides.

4. The package of claim 1 and wherein one of said sides includes the junction of the overlying front and back portions of a sheet, with an edge of the back portion spaced slightly from the edge of the front portion so as to facilitate the separation of the edges of the front and back portions of the sheet to admit the syringe nozzle to the frangible portion which is located adjacent said sheet edges.

* * * * *